United States Patent [19]

Scherr

[11] 4,100,268

[45] Jul. 11, 1978

[54] PREPARATION OF GENTAMICIN SENSITIZED PARTICLES FOR AGGLUTINATION TESTS

[75] Inventor: George H. Scherr, Park Forest, Ill.

[73] Assignee: Technam, Inc., Park Forest South, Ill.

[21] Appl. No.: 664,506

[22] Filed: Mar. 8, 1976

[51] Int. Cl.$^2$ .................... A61K 39/00; G01N 31/00; G01N 33/16

[52] U.S. Cl. .................... 424/12; 23/230 B; 260/8; 260/112 R; 260/112 B; 260/121; 424/8; 424/88

[58] Field of Search .................... 424/8, 12, 85, 88; 23/230 R, 230 B; 260/6, 8, 112 R, 112 B, 121

[56] References Cited

U.S. PATENT DOCUMENTS

| 3,639,558 | 2/1972 | Csizmas | 424/12 |
| 3,652,761 | 3/1972 | Weetall | 424/12 |
| 3,775,536 | 11/1973 | Spector | 424/1 |
| 3,951,748 | 4/1976 | Devlin | 424/12 X |

FOREIGN PATENT DOCUMENTS 1,402,427  8/1975  United Kingdom.

OTHER PUBLICATIONS

Kabat, Exptl. Immunochem., C. C. Thomas, Springfield, Ill., pp. 97–99, 120–124.
Lee, Clin. Chem., vol. 21, No. 7, 1975, p. 967, Ab. 140.
Broughton, Clin. Chem., vol. 21, No. 7, 1975, p. 968, Ab. 142.
Lewis, Nature, New Biol., vol. 239, Oct. 18, 1972, pp. 214–216.
Gross, Immunochem., vol. 11, 1974, pp. 453–456.
Wainer, Sci., vol. 176, 1972, pp. 1143–1144.

*Primary Examiner*—Albert T. Meyers
*Assistant Examiner*—A. P. Fagelson
*Attorney, Agent, or Firm*—Kinzer, Plyer, Dorn & McEachran

[57] ABSTRACT

Detection of gentamicin is made possible by preparing an analytical body comprising a macromolecule which carries gentamicin, attached to a particle.

16 Claims, No Drawings

PREPARATION OF GENTAMICIN SENSITIZED PARTICLES FOR AGGLUTINATION TESTS

The antibiotic gentamicin is a member of the amino glycoside group of antibacterial agents. The clinical characteristics of this antibiotic have been described (AMA Drug Evaluations, 1973, 2nd Ed., Publ. Science Group, Inc., Aston, Mass., p 569–570). Gentamicin can cause serious renal damage and recommendations have been made that the serum concentration in excess "of 12 $\mu$g/ml are generally considered to be hazardous" (ibid, pg. 570). Because the mean half-life of gentamicin after an intramuscular injection may be no more than approximately 2 hours, most of the antibiotic being excreted in the urine unchanged, it has become necessary, in order to maintain therapeutic doses and also to avoid reaching toxic levels (Progress in Antimicr. and Anti Cancer Chemotherap., Proc. 6th Int. Cong., Chemotherapy, Univ. Park Press., Balt., Md., 1970, pp 673–676, 540–542, 811–814) to monitor the blood serum levels by microbiological assay (Am. J. Med. Tech., March, 1975, p 12–13). The microbiological assay may require anywhere from 14-24 -hours for a determination and is rather laborious. A more serious complication has to do with the fact that many patients under therapy may have been treated with antibiotics other than gentamicin and any residual remaining of such antibiotics could alter the assay presumably done solely for gentamicin. Thus other criteria of clinical toxicity have to be relied upon in order to assess a potentially sudden dangerous rise in blood level, such as creatinine clearance and/or other criteria of impaired renal function. A radioimmunoassay test for gentamicin has been developed (Mahon et al., Antimicrobiol Agents Chemotherap., 3:585–89, 173) which is less time-consuming but requires the use of radio-isotopes and the necessary restraints imposed by their use.

The hemagglutination-inhibition test for gentamicin assay in blood serum and other body fluids is herein described and provides laboratory data in approximately 1-1½ hours after the blood specimen has been procured from the patient.

Preparation of Antigen

To 8 ml of a solution of gentamicin sulfate containing 50 mg gentamicin per ml, add 100 mg of bovine serum albumin (BSA) (Sigma, Kohn fraction II). To the above add 500 mg of 1-ethyl-3-(-3-dimethyl-aminopropyl)-carbodiimide hydrochloride (CDI) and adjust the pH of the solution to 5.2 utilizing either 0.1 N NaOH or 0.1 N HCl. The BSA or other macromolecule similarly utilized may be considered the carrier protein.

Incubate the reaction mixture at room temperature overnight. The mixture should then be concentrated approximately 5-fold utilizing an Amicon ultrafiltration cell and a PM-30 membrane; the ultrafiltration should be done in the cold at approximately 3° C. Dialyze the concentrated reaction mixture against distilled water in the cold for approximately 2 days while effecting at least 2-3 changes of distilled water per day. The dialyzed material should then be stored frozen until used.

Immunization Procedure

The gentamicin-BSA conjugate prepared as above in a concentration of 4 mg/ml (utilizing the protein concentration as the determination of weight) is mixed and emulsified with an equal volume of Complete Freunds Adjuvant and the mixture injected intramuscularly into rabbits once a week on the following schedule:

| Day 1 | 2.0 ml | instramuscularly |
| --- | --- | --- |
| 8 | 2.0 ml | " |
| 15 | 2.0 ml | " |
| 22 | 2.0 ml | " |
| 29 | 1.0 ml | " |
| 36 | 1.0 ml | " |
| 46 | Trial bleeding | |

Antibody of gentamicin may be detected approximately six weeks after the initial immunization injection.

Sensitizing Sheep Red Blood Cells (SRBC)

EXAMPLE 1

Normal sheep blood is collected in an equal volume of Alsevers solution. The cells are washed twice with saline by centrifugation in the cold (5° C) at 1700 rpm for 10 minutes and once with phosphate buffer saline at pH 7.3 (PBS). To 1 ml of packed cells washed as above, 40 ml of PBS 7.3 is added to result in a final erythrocyte concentration of 2.5%. Equal volumes of the 2.5% SRBC suspension and a 1:20,000 dilution of tannic acid in saline are mixed and incubated at 37° C for 10 minutes. This incubation is effected with shaking or stirring; the tannic acid must be prepared fresh each time. The cells thus tanned are then centrifuged at 5° C at 1700 rpm for 10 minutes and washed twice with PBS 7.3. The washed cells are now resuspended to their original volume to result in a 2.5% cell suspension and may then be kept refrigerated at 5° C but should be utilized within 24 hours.

The tanned cells prepared as above are coated with the gentamicin-BSA by adding the following:

| Flask No. | I | II (control |
| --- | --- | --- |
| Tanned SRBC 2.5% | 3.0 ml | 3.0 ml |
| PBS pH 6.4 | 11.5 ml | 11.5 ml |
| Gentamicin - BSA (1 mg/ml) | 0.5 ml | — |
| Dialyzed BSA (1 mg/ml) | — | 0.5 ml |

These flasks are shaken or stirred by magnetic stirrer for 10 minutes at room temperature, the cells are then centrifuged at 1700 rpm for 10 minutes at 5° C and washed twice by repeated centrifugation with PBS pH 7.3 containing 1% normal rabbit serum (NRS 100).

The cell preparations in flasks I and II are then titrated with anti-gentamicin serum. The serum procured from the blood of the immunized rabbit is first absorbed with a quantity of BSA which has been CDI-treated in a manner as was done with the CDI-treated gentamicin - BSA. Thus, 1 ml of rabbit serum is mixed with 19 ml of CDI-treated BSA at a concentration of 1 mg/ml (of BSA) and the mixture allowed to stand at refrigeration temperature for 2 hours. After this period the absorbed serum is centrifuged at 5000 rpm for 30 minutes at 5° C in order to remove any precipitates. The purpose of the absorption with the CDI-treated BSA is to remove any antibodies from the rabbit serum to the BSA protein.

The serial dilutions of the absorbed anti-gentamicin serum and gentamicin sensitized tanned SRBC is performed as follows utilizing zero, 10, and 50 nanograms of gentamicin per ml of PBS 7.4 as inhibitors.

The test to demonstrate the utility of the gentamicin-sensitized cell is performed in a microtiter-type tray with "V" wells (Linbro, New Haven, CT 27611). The absorbed antiserum constituting the 1:20 dilution of the rabbit anti-gentamicin serum is further serially diluted twofold to result in a series of dilutions of 1:20, 1:40, 1:80 etc. up to and including 1:1280. One drops of PBS pH 7.4 containing 1% normal rabbit serum is added to a series of 8 wells in such a titer tray and in a second row, one drop of a solution of standard Gentamicin containing 10 nanograms per ml is added. In a third row of 8 wells one drop is placed into each well of a standard solution of gentamicin containing 50 ng/ml. To each of the first three wells vertically is now added one drop of the 1:20 diluted antiserum, into the second three wells is added one drop of the 1:40 diluted antiserum, in the third series of wells is added one drop of the 1:80 dilution of antiserum, etc., except that in the eighth well one drop of phosphate buffer saline containing 1% normal rabbit serum is added as a control. The tray is permitted to stand for approximately 3-5 minutes so that any reaction between the antiserum and gentamicin is permitted to take place and then two drops of gentamicin sensitized cells, prepared as described above, is added to every one of the 24 wells.

After 1 hour of standing one should expect to find the following:

If there is no gentamicin present, then the antiserum is free to react with the gentamicin sensitized to the red blood cells. Such a reaction will cause the cells to agglutinate and they will not settle in a pellet. If there is no antibody present the cells will settle in a pellet as will also occur in the 'controls' which contain no antiserum. Where zero gentamicin was used as a standard the titer of the antibody for the gentamicin-sensitized cells is between 1:160 and 1:320.

Ten (10) nanograms/ml (ng/ml) of gentamicin inhibit an amount of antibody so that the titer of the antiserum is 1:80; the addition of 50 ng/ml inhibits the antiserum still further and the pellet comes down in the vertical row of the 1:40 dilution of the antiserum. This clearly indicates the specific inhibitory effect of the gentamicin in reacting with the anti-gentamicin sera, and also indicates the feasibility of performing a quantitative test for the detection of gentamicin in body fluids or other solutions where gentamicin assay might be desirable.

The purpose of repeating such an experiment with the contents of Flask 2 above containing solely the absorbed BSA is to demonstrate that all of the antiserum that might be present in the anti-gentamicin serum that could react with the protein carrier (BSA) coupled to the gentamicin has been absorbed, and therefore is not an interfering factor in the interpretation of the test results just described.

The proportion of other reagents to gentamicin-BSA is not critical and variations in these proportions are feasible which still permit the preparation of suitably-sensitized cells for performing the test as described above in Example 1.

EXAMPLE 2

The following proportions of tanned sheep red blood cells, PBS pH 6.4, and gentamicin-BSA were utilized in Flasks No. I and II.

Flask III again represents a control to determine that anti-gentamicin serum was completely absorbed in its anti-BSA activity.

| Flask No | I | II | III (control) |
|---|---|---|---|
| Tanned SRBC 2.5% | 3.0 ml | 3.0 ml | 3.0 ml |
| PBS pH 6.4 | 11.0 ml | 11.9 ml | 11.0 ml |
| Gentamicin - BSA (0.2 mg/ml) | 1.0 ml | 0.1 ml | — |
| BSA (0.2 mg/ml) | — | — | 1.0 ml |

The cells were treated after the sensitization exactly in the same manner as outlined in Example I above and a repetition of the experiment outlined therein resulted in essentially similar results.

Other methods of coating the red blood cells with gentamicin-BSA can be utilized and these were performed as described in the following example:

EXAMPLE 3

The following ingredients were mixed with stirring while the reaction flask was kept cold in an ice bath:

| Flask No. | I | II |
|---|---|---|
| Gentamicin - BSA (1.2 mg/ml) | 4.0 ml | 3.0 ml |
| SRBC 5% | 16.0 ml | 16.0 ml |
| PBS pH 7.3 | 26.0 ml | 27.0 ml |
| Dialyzed BSA (1 mg/ml) | 15.0 ml | 12.5 ml |
| Bis-diazobenzedine (1:15 dilution) | 9.0 ml | 9.0 ml |

After 12 minutes of stirring at room temperature the mixture was spun in a centrifuge at 1700 rpm for 7 minutes at 5° C and the supernatent discarded. The cells were washed two more times with phosphate buffered saline pH 7.3 and the cells finally suspended to a final concentration of 3% in the PBS pH 7.3.

The cells were immediately placed in a beaker with a stirring bar and a volume of 37% formaldehyde solution equal to 1/5th the volume of the total blood cell suspension was added. The addition takes place with constant stirring and the reaction mixture is left to stand overnight at 5° C.

After this period of time the cells are centrifuged at 1700 rpm for 10 min. and at 50C and resuspended in PBS pH 7.3. The cells are then washed and centrifuged a total of three times with the final cell pellet being resuspended in PBS pH 7.3 containing 1% of normal rabbit serum and merthiolate in a final concentration of 1:10,000. These fixed, covalently diazitized cells are then tested against rabbit anti-gentamicin serum as shown in Example 1 above. The results were essentially similar to those found with gentamicin-BSA tanned cells. The advantage of utilizing a bis-diazobenzidine coupling agent as described in Example 3 stems from the fact that this treatment results in a covalent bond between the protein carrier of the gentamicin and the protein coat of the sheep red blood cells and such a covalent bond results in a more stable preparation than the utilization of tanned cells onto which surface the gentamicin-BSA is merely adsorbed.

The purpose of the formalin treatment of the cells is merely to harden the cell surface and make it a little more stable for prolonged storage on the shelf. Otherwise, unpreserved cells would also perform essentially as well except for the factor of stability with prolonged storage.

A typical assay protocol as it can be practiced for clinical or other specimens is illustrated by the following example:

EXAMPLE 4

| Use serum diluted 31 × (0.1 ml serum + 3.0 ml Reagent Diluent, code #67-97-7) | Label Tube #1 | Use dispenser so that 1 drop = .05 ml (50 μl) |
|---|---|---|

Step 1

Dispense 3.0 ml of Reagent Diluent into 6 small tubes; number tubes 2 to 7. Dispense the number of drops from tube No. 1 into the tubes Nos. 2–7 using serum diluted as above. Make sure the tubes are thoroughly mixed; do not use a vortex mixer.

| Tube No. | Add No. of Drops of Diluted Serum | Agglutination at this dilution Equals Concentration in serum of (μg/ml) |
|---|---|---|
| 1 |    | .31 |
| 2 | 12 | 1.86 |
| 3 | 7  | 2.97 |
| 4 | 4  | 4.96 |
| 5 | 3  | 6.51 |
| 6 | 2  | 9.61 |
| 7 | 1  | 18.9 |

Step 2

Using disposable Pasteur pipettes, add one drop from tube No. 1 into the first well. Add one drop from tube No. 2 into the second well, etc. Add one drop gentamicin standard containing 10 ng/ml to well No. 8. Add 2 drops of NRS 100 to well No. 9.

Add one drop of reconstituted antiserum to all of the wells except No. 9.

Step 3

Insure thorough mixing of the reagents by gently tapping the tray on the bench surface (vertical) and by rotating it gently on the bench (horizontal). Led stand at room temperature for 5–10 minutes.

Step 4

GENTAMICIN SENSITIZED RED BLOOD CELLS

Just prior to use, shake vial to suspend cells. Centrifuge contents or an aliquot at approximately 1700 rpm for about 10 minutes, pour off and discard supernatant. Add an amount of NRS 100 Diluent exactly equal to the amount of supernatant discarded. Use a Pasteur pipette to prepare uniform cell suspension by repeated and forceful pipetting. The cells kept on the bench during these operations and during use are best kept in an ice bath.

Using disposable Pasteur pipettes add 2 drops gentamicin sensitized red blood cells appropriately reconstituted to all the wells (Nos. 1–9).

Step 5

Insure thorough mixing of the reagents by the procedure described in Step 3. Let stand on table top at room temperature for 60–90 minutes, after which the results may be read. The trays may be stacked and the top tray should be protected with a plastic sheet to avoid evaporation — or an empty tray can be stacked on top to reduce evaporation. The test has been calibrated for use at a relatively wide range of ambient temperatures from 20° C–27° C.

The reactions of the test are quite stable so that, in the event of delay in reading the test results after 90 minutes, the results will remain the same even after a few days.

READING OF RESULTS:

The number of well which shows a pellet of cells equal to that of the control (Tube NO. 8) is the endpoint and the micrograms of gentamicin per ml of sample should be read in the column opposite that tube number. The well No. 9 is a control of the cells which must come down as a pellet (absence of agglutination).

Utilizing above procedure, patient's serum was assayed both by microbiological and the hemagglutination inhibition test described above. The results were as follows:

| Patient | Hemagglutination Inhibition Test | Microbiological Assay |
|---|---|---|
| 1  | 6 ng/ml     | 5.3    |
| 2  | 3 ng/ml     | 2.0    |
| 3  | 6 ng/ml     | 5.6    |
| 4  | 3 ng/ml     | 5.0    |
| 5  | 6 ng/ml     | 3.5    |
| 6  | 6 ng/ml     | 4.2    |
| 7  | < .75 ng/ml | < 1.25 |
| 8  | 3 ng/ml     | 1.55   |
| 9  | 3 ng/ml     | 2.1    |
| 10 | 3 ng/ml     | 2.6    |
| 11 | 3 ng/ml     | 2.7    |
| 12 | 6 ng/ml     | 3.5    |

The above results are to be considered the same within the experimental error of the methods utilized.

It is quite clear from the above data that we have invented a novel method of detecting and quantitating gentamicin whether present in body fluids or in other media. The determinations can be achieved with minimal equipment and in a relatively short period of time to provide data indicative of the blood levels of gentamicin in patients under therapy. Although bovine serum albumin was utilized in these experiments as the protein carrier for the gentamicin, whether injected into animals in order to produce antibody or utilized for adsorption or bonding to a cell, it is clear that the bovine serum albumin is acting in this case merely as a macromolecular carrier of the hapten gentamicin and therefore any other appropriate carrier of which there are many known in the profession could be utilized without deviating from the novelty of the invention described herein.

EXAMPLE 5

The following ingredients in the volumes and proportions indicated were mixed in a flask which was kept cold in an ice bath with continuous stirring.

| | |
|---|---|
| gentamicin-Goat Gamma globulin (0.2 mg/ml) | 0.8 ml |
| Dialyzed BSA (1 mg/ml) | 1.5 ml |
| 5% SRBC | 3.2 ml |
| PBS pH 7.3 | 1.2 ml |
| Bis-diazobenzidine(1:15 dil) | 1.8 ml |

After 12 minutes of stirring at room temperature the mixture was spun in a centrifuge at 1700 rpm for 7 minutes at 5° C and the supernatant discarded. Then the cells were worked up exactly as described in the Example 3 above including the formalin.

These cells now covalently bonded with gentamicin-goat gamma globulin to preserved sheep red blood cells were tested against rabbit anti-gentamicin serum as indicated in Example 1 above with similar results.

The red blood cells utilized in the examples given are considered 'passive' in that they do not play any direct role in the agglutination reaction; they are merely a carrier by adsorption or covalent bonding of the hapten or antigen contained on their surface. Almost any cell may be utilized onto whose surface the gentamicin protein carrier may be either adsorbed or covalently bonded. For example, microbial cells such as yeast cells have been utilized in an experiment as outlined above in Experiment 3 for sheep red blood cells with essentially similar results and without deviating from the basic novelty of the invention described herein. In fact, it is not necessary to utilize viable cells if polymer particles such as those of latex or polystyrene are used onto whose surface the hapten-macromolecular complex can be adsorbed. If the inert polymer particles have determinant groups such as — COOH or — NH$_2$ groups they could be utilized for covalent bonding to the protein carrier of the gentamicin by the utilization of carbodiimide or diazatization with bix-diazobenzidine as described in Example 3 above. Although bis-diazo benzidine was utilized here as an example of covalent bonding between the carrier protein carrying the hapten gentamicin in the surface of the red blood cell, it is clear that other covalent bonding techniques such as carbodiimide, which is well-known in the profession, can be utilized as long as the particle to which the hapten macromolecular carrier used to be covalently bonded has determinant groups that would lend itself to the preparation of a covalent bond between molecules present on the protein of the carrier protein and the surface of the cell or other particle.

One significant criterion which should govern the choice of particle is their size so that they lend themselves to either direct or indirect agglutination and can be made visible on a slide or in an indirect agglutination test as described above in a well-tray or performed in a test tube.

SUMMARY

An outline of the procedure we have developed may be depicted as follows:

Step One: Prepare a macromolecule covalently bonded to gentamicin where the macromolecule may be bovine serum albumin.

Step Two: Inject the gentamicin-macromolecule complex thus prepared utilizing animals and an appropriate injection schedule.

Step Three: Harvest the serum from animals thus injected to procure anti-gentamicin antibodies after absorbing the serum with bovine serum albumin or other carrier protein.

Step Four: Prepare fixed red blood cells to which has been adsorbed or covalently bonded the gentamicin-macromolecule complex.

Step Five: The absorbed antiserum is then titrated against free gentamicin in a welled tray or small tube to which is added the sensitized preserved red blood cells which will agglutinate in the absence of gentamicin (leave uncoupled the anti-gentamicin serum) or the cells will settle (not agglutinate) in the absence of anti-gentamicin serum resulting from the free gentamicin in the sample, neutralizing all of the anti-gentamicin serum. serum.

We claim:

1. A process for the preparation of an agglutinable gentamicin-macromolecule-carrying particle which process comprises covalently coupling gentamicin to a protein with a carbodiimide derivative and adsorbing or covalently coupling the resultant gentamicin-protein moiety to washed red blood cells, resulting in a particle consisting essentially of the protein, the red blood cell and coupled gentamicin.

2. A process as claimed in claim 1 in which the red blood cells are preserved with formaldehyde.

3. A process as claimed in claim 1 in which the red blood cells are sheep red blood cells.

4. A process as claimed in claim 1 in which the gentamicin-macromolecule moiety is adsorbed to red blood cells which have been treated with tannic acid.

5. A process as claimed in claim 1 in which the protein to which Gentamicin is covalently coupled is bovine serum albumin.

6. A process as claimed in claim 1 in which the protein to which gentamicin is covalently coupled is goat gamma globulin.

7. A process as claimed in claim 1 in which the gentamicin-protein moiety is covalently coupled to the red blood cells with bisdiazobenzidine.

8. A process for the preparation of an agglutinable gentamicin-macromolecule-carrying particle which process comprises covalently coupling gentamicin to a protein with a carbodiimide derivative and adsorbing or covalently coupling said gentamicin-protein moiety to microbial cells.

9. A process as claimed in claim 8 in which the microbial cells are yeast cells.

10. A process as claimed in claim 8 in which the gentamicin-macromolecule moiety is covalently coupled to the yeast cells with bisdiazobenzidine.

11. A process as claimed in claim 8 in which the macromolecule to which gentamicin is covalently coupled is bovine serum albumin.

12. A process as claimed in claim 8 in which the microbial cells are preserved with formaldehyde.

13. A process for the preparation of an agglutinable gentamicin-macromolecule-carrying particle which process comprises covalently coupling gentamicin to a protein with a carbodiimide derivative and adsorbing or covalently coupling said gentamicin-protein moiety to inert polymer particles.

14. A process as claimed in claim 13 in which the macromolecule to which gentamicin is covalently coupled is bovine serum albumin.

15. A process as claimed in claim 13 in which the protein to which the gentamicin is covalently coupled as goat gamma globulin.

16. A process as claimed in claim 13 in which the gentamicin-protein moiety is covalently coupled to inert polymer particles with bisdiazobenzidine.

* * * * *

UNITED STATES PATENT AND TRADEMARK OFFICE
CERTIFICATE OF CORRECTION

PATENT NO. : 4,100,268
DATED : July 11, 1978
INVENTOR(S) : George H. Scherr

It is certified that error appears in the above—identified patent and that said Letters Patent are hereby corrected as shown below:

On the title page, the following should be deleted:

[73] Assignee: Technam, Inc., Park Forest South, Ill.

Signed and Sealed this

Sixteenth Day of January 1979

[SEAL]

Attest:

RUTH C. MASON
Attesting Officer

DONALD W. BANNER
Commissioner of Patents and Trademarks